United States Patent

Yu et al.

[11] Patent Number: 6,080,323
[45] Date of Patent: Jun. 27, 2000

[54] METHOD OF REMOVING BIOFILMS FROM SURFACES SUBMERGED IN A FOULED WATER SYSTEM

[75] Inventors: F. Philip Yu; Anthony W. Dallmier, both of Aurora, Ill.

[73] Assignee: Nalco Chemical Company, Naperville, Ill.

[21] Appl. No.: 09/251,614

[22] Filed: Feb. 17, 1999

[51] Int. Cl.[7] .................................................. C02F 1/50
[52] U.S. Cl. ......................... 210/758; 210/754; 210/764; 162/161; 510/422; 514/25; 514/738; 422/28
[58] Field of Search ........................ 162/161; 210/754, 210/755, 756, 758, 764; 510/422; 514/25, 738; 422/28, 36, 37

[56] References Cited

U.S. PATENT DOCUMENTS

| | | | |
|---|---|---|---|
| 4,976,874 | 12/1990 | Gannon et al. | 210/755 |
| 5,512,186 | 4/1996 | Wright et al. | 210/764 |
| 5,877,132 | 3/1999 | Callaghan et al. | 510/114 |
| 5,965,513 | 10/1999 | Allan et al. | 510/422 |
| 5,994,286 | 11/1999 | Desai et al. | 510/386 |

*Primary Examiner*—Peter A. Hruskoci
*Attorney, Agent, or Firm*—Kelly L. Cummings; Thomas M. Breininger

[57] ABSTRACT

A method is disclosed for removing biofilms from surfaces submerged in a fouled water system by adding to the water system an alkyl polyglycoside having the chemical formula:

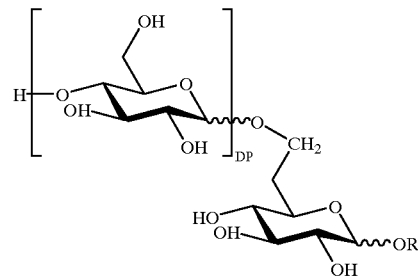

wherein R is a $C_8$–$C_{16}$ alkyl chain and DP is from 0 to 3 carbohydrate units.

19 Claims, No Drawings

METHOD OF REMOVING BIOFILMS FROM SURFACES SUBMERGED IN A FOULED WATER SYSTEM

FIELD OF THE INVENTION

This invention relates generally to the field of water treatment technologies and, more particularly, to a method of removing biofilms from surfaces submerged in a fouled water system.

BACKGROUND OF THE INVENTION

Biofouling has always been problematic in industrial water systems such as cooling towers, heat exchangers and air washers, because it can adversely affect heat transfer efficiency and fluid frictional resistance, thereby subsequently reducing production rates. In addition, biofouling also plays an important role in microbiologically influenced corrosion.

The presence of microorganisms in industrial waters cannot be totally eliminated, even with the excessive use of chemical biocides. The most common way to control biofouling is through the application of toxic chemical biocides such as chlorine, bromine, isothiazolones, glutaraldehyde or other antimicrobials. These biocides are added in an attempt to kill both planktonic and attached microorganisms.

Some microorganisms attach to inert surfaces forming aggregates with a complex matrix consisting of extracellular polymeric substances (EPS). This consortium of attached microorganisms and the associated EPS is commonly referred to as a biofilm. Biocides have difficulty penetrating biofilms and removing them from surfaces. Although excessive biocide dosages may be able to control biofouling, the presence of biocides in effluent waters is usually environmentally unacceptable.

Mechanical treatments including scrapers, sponge balls, or "pigs" are also commonly used to remove biofilms. Acids, chelants and dispersants are likewise considered to be effective in causing the detachment of deposited materials. In addition, sidestream filtration devices, which continuously process 1–5% of the system water, have drawn increased interest lately. Nevertheless, these approaches are either too labor intensive and/or expensive.

Dispersants are sometimes applied along with biocides to enhance antimicrobial efficacy in industrial waters. The dispersants used in these applications will hereinafter be referred to as "biodispersants." Most biodispersants currently available on the market, such as block copolymer or terpolymer, have high molecular weights ranging from 1,000 to 15,000,000. These biodispersants attract fine foulant particles onto polymeric chains and form fluffy particles that are more readily detached from the fouled surfaces. It is also believed that these surface active compounds can increase the diffusion of biocide into the biofilm, and subsequently cause biofilm detachment.

To date, biodispersants have not been used effectively without supplementation with biocides. As the United States Environmental Protection Agency (EPA) regulations and global concerns of biocide usage become more prevalent, high performance biodispersants having low toxicity are needed to control biofouling either with or without the addition of chemical biocides.

Accordingly, it would be desirable to provide a method of removing biofilms from surfaces submerged in water using a biodispersant which is effective both alone and with the use of a biocide. It would also be desirable to utilize a biodispersant which is biodegradable and has a low toxicity. It would furthermore be desirable to employ a biodispersant which does not affect corrosion and scale inhibition programs used in industrial water treatment.

SUMMARY OF THE INVENTION

The method of the invention calls for adding to a fouled water system an alkyl polyglycoside having the chemical formula:

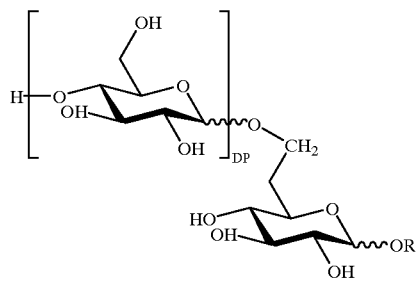

wherein R is a $C_8$–$C_{16}$ alkyl chain and DP is from 0 to 3 carbohydrate units.

This method efficiently and effectively removes biofilms from surfaces submerged in the fouled water system. The method is also environmentally acceptable and economically appealing because the use of biocides can be minimized or eliminated, and the biodispersant utilized in the practice of the invention is biodegradable and has a low toxicity. Moreover, the method does not affect corrosion and scale inhibitor programs used in industrial water treatment.

DETAILED DESCRIPTION OF THE INVENTION

The present invention is directed to a method of removing biofilms from surfaces submerged in a fouled water system. In accordance with this invention, an alkyl polyglycoside (APG) having the chemical formula:

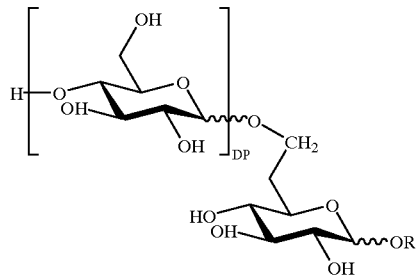

wherein R is a $C_8$–$C_{16}$ alkyl chain and the degree of polymerization (DP) is from 0 to 3 carbohydrate units, is added to the water system. Preferably, the alkyl chain is linear and the DP is from about 1.1 to 1.5.

Glucopon® 225 and Burco® NPS-225 ($C_8$, $C_{10}$), Glucopon® 425 ($C_8$–$C_{16}$) and Glucopon® 600 and 625 ($C_{12}$–$C_{16}$) are commercially-available APG products which may be used in the practice of the invention. (The Glucopon® products are available from Henkel Corporation of Ambler, Pa. and the Burco® product is available from Burlington Chemical Co., Inc. of Burlington, N.C.). It is believed that other APG products from other suppliers can also be used in the practice of the present invention.

It is preferred that the amount of APG which is added to the water system be in the range of about 0.1 ppm to about 10 ppm based on active ingredient, with about 1 ppm to about 10 ppm being most preferred. APG can be added to the water system by any conventional method, i.e., by slug, intermittently or continuously.

A biocide may also optionally be added to the water system in accordance with the practice of this invention. The biocide may be added by any conventional method either separately or in combination with APG. The biocides which may be used in the practice of the present invention include oxidizing biocides such as chlorine-based biocides, bromine-based biocides, peracetic acid, hydrogen peroxide and ozone; and non-oxidizing biocides such as isothiazolone, glutaraldehyde and quaternary amine compounds. The amount of biocide added to the water system is dependent upon the particular water treatment application and is generally known to those skilled in the art. However, it should be noted that the required amount of biocide is minimized when used in combination with APG.

In accordance with the method of this invention, biofilms are removed from all types of submerged surfaces, e.g., glass, metals, wood and plastics.

The method of the present invention may be used in an industrial water system or a recreational water system. The types of industrial water systems in which APG can be employed include, but are not limited to, cooling water systems, air washers, evaporative condensers, pasteurizers, air scrubbers, produce sanitizer streams, fire protection water systems and heat exchanger tubes.

The types of recreational water systems in which APG can be utilized include, but are not limited to, decorative fountains and full-body immersion systems such as swimming pools, spas and hot tubs.

The present invention takes advantage of the detergency and dispersancy of APG for use as a biodispersant. It was surprisingly found that when APG was added to a fouled water system, biofilms were effectively removed from the submerged surfaces. The APG biodispersant described herein exhibited superior performance as compared to other commercially-available biodispersants, and biofilm removal was achieved both with and without the addition of chemical biocides. It should be noted that when APG is used, lower amounts of toxic biocides are needed to achieve the same level of control. In addition, APG offers a low or non-toxic means to control biofouling and APG is biodegradable, thereby providing an environmentally-acceptable approach to water treatment. Moreover, the use of APG does not affect corrosion and scale inhibitor programs used in industrial water treatment.

EXAMPLES

The following examples are intended to be illustrative of the present invention and to teach one of ordinary skill how to make and use the invention. These examples are not intended to limit the invention or its protection in any way.

The biofilms used in the following Examples were generated from a mixed microbial consortium isolated from a cooling water deposit. The devices used to house the test bacterial biofilms were continuous flow stirred tank bioreactors. Both laminar and turbulent flow conditions were tested for product performance. Synthetic cooling water [400 ppm Ca, 200 ppm Mg, 400 ppm M alkalinity (all based on $CaCO_3$)] was used as make-up for the bioreactors. Bacterial biofilms were grown on glass and stainless steel surfaces for 96 hours at room temperature in order to reach steady state conditions. The thickness of the biofilms was approximately 500 $\mu$m.

The biofilms were then treated by continuously applying biodispersant for 24 hours in an attempt to remove the biofilms from the substrata. The area densities of the bacterial biofilms were measured with a protein assay. The biomass was expressed as $\mu$g protein per $cm^2$. The effectiveness of biofilm removal was determined by biomass loss during the treatment period. Conventional plate counts on tryptone glucose extract (TGE) agar were also employed to measure the viability of the bacterial population. The viable cell density of the biofilm bacteria was expressed as colony forming units (CFU) per $cm^2$ biofilm.

Example 1

Several surfactants were tested in laboratory biofilm reactors to evaluate their biofilm removal activities. Biomass removal activities of the biodispersants against bacterial biofilms were measured after 24 hours of continuous treatment. The APG tested was Glucopon® 425 (a mixture of $C_8$, $C_{10}$ and $C_{12-16}$), a nonionic surfactant. NALCO® 7348, a nonionic ethylene oxide/propylene oxide (EO/PO) block copolymer, was also evaluated. The anionic surfactants used in this example were diphenyl disulfonate (Dowfax® available from Dow Chemical Company of Midland, Mich.), linear alkylbenzene sulfonate (LAS) and sodium octane sulfonate. A commercial biofilm cleaning product sold under the name Ultra-Kleen (available from the Sterilex Corporation of Owing Mills, Md.) was tested. A cationic surfactant, dimethyl amide polymer (DMAD), commercially sold by Buckman Laboratories, of Memphis, Tenn. was also included in this example. As shown below in Table 1, the biofilm removal for APG was significantly higher than for any of the other products tested.

TABLE 1

| Biodispersant | Active Ingredient (ppm) | % Biomass Removal (protein as $\mu$g/cm$^2$) | Log Reduction of Viable Biofilm Bacteria (CFU/cm$^2$) |
|---|---|---|---|
| APG | 10 | 46.15 | 0.13 |
| EO/PO copolymer (NALCO ® 7348) | 10 | 0.00 | 0.00 |
| diphenyl disulfonate | 10 | 2.16 | 0.00 |
| sodium octane sulfonate | 50 | 0.00 | 0.09 |
| sodium octane sulfonate | 100 | 29.62 | 0.22 |
| Ultra-Kleen | 1000 | 39.36 | 1.83 |
| 13.3% LAS | 100 | 0.00 | 0.00 |
| DMAD | 100 | 0.00 | 0.10 |

Note that a zero value was assigned if the attached biomass or the viable bacteria levels increased in the bioreactor. This phenomenon occurred if the biodispersant was ineffective.

Example 2

The effects of APG on corrosion rates were conducted with 4.5 ppm sodium tolyltriazole, 20 ppm 2-phosphonobutane-1,2,4-tricarboxylic acid (PBTC) and 18 ppm terpolymer of acrylic acid/acrylamide/sulfomethylacrylamide. The test water chemistry and alkalinity were maintained at 360 ppm $CaCl_2$, 200 ppm $MgSO_4$ and 220 ppm $NaHCO_3$. The pH was maintained at 8.7 and the temperature was set at 55° C. The APG concentration was 10 ppm. The tests were run in duplicate for 40 hours, and the corrosion rates were determined by electrochemical parameters. The addition of APG did not adversely affect corrosion control, as indicated by the low corrosion rates shown below in Table 2.

TABLE 2

| APG Addition (ppm active ingredient) | Reaction Time (hours) | Corrosion Rate (mpy) |
|---|---|---|
| 0 | 5 | 0.4 |
| 10 | 5 | 0.3 |
| 0 | 10 | 0.5 |
| 10 | 10 | 0.3 |
| 0 | 25 | 0.8 |
| 10 | 25 | 1.4 |
| 0 | 40 | 1.3 |
| 10 | 40 | 1.8 |

Example 3

The effects of APG on scale formation were evaluated. Scale formation was determined by solubility stress test which was run at 50° C. The scale inhibitors used in this study were 1-hydroxyethylidene-1,1-diphosphonic acid (HEDP) and 2-phosphonobutane-1,2,4-tricarboxylic acid (PBTC).

The scale formation, indicated by the low percent recovery of soluble $Ca^{2+}$ after two hours, was slightly higher at 400 ppm $CaCO_3$ or $Ca^{2+}/HCO_3$ with 10 ppm APG in the system. APG did not affect scale formation when the calcium levels were raised to 600 ppm. Overall, as shown in Table 3, there was no significant difference on the scale formation either with or without APG applied at 10 ppm.

TABLE 3

| ppm as $CaCO_3$ $Ca^{2+}/HCO_3$ | ppm HEDP | ppm PBTC | ppm APG | pH | Percent Recovery of Soluble $Ca^{2+}$ |
|---|---|---|---|---|---|
| 300 | 5 | 0 | 10 | 7.8 | 32 |
| 300/300 | 0 | 10 | 10 | 7.9 | 103 |
| 300/300 | 5 | 0 | 0 | 8.1 | 47 |
| 3001300 | 0 | 10 | 0 | 8.1 | 101 |
| 400 | 5 | 0 | 10 | 8.0 | 38 |
| 400/400 | 0 | 10 | 10 | 8.1 | 81 |
| 400/400 | 5 | 0 | 0 | 8.1 | 37 |
| 400/400 | 0 | 10 | 0 | 8.3 | 45 |
| 500 | 5 | 0 | 10 | 8.2 | 25 |
| 500/500 | 0 | 10 | 10 | 8.0 | 42 |
| 500/500 | 5 | 0 | 0 | 7.9 | 21 |
| 500/500 | 0 | 10 | 0 | 8.0 | 33 |
| 600 | 5 | 0 | 10 | 7.5 | 9 |
| 600/600 | 0 | 10 | 10 | 8.0 | 10 |
| 600/600 | 5 | 0 | 0 | 8.0 | 12 |
| 600/600 | 0 | 10 | 0 | 8.1 | 28 |

Example 4

Synergism between APG and a stabilized bromine-based oxidizing biocide was determined with the calculation described by F. C. Kull, P. C. Eisman, H. D. Sylwestrowicz and R. L. Mayer, Applied Microbiology, vol. 9, pages 538–541, (1961) using the relationship:

$$\frac{Q_A}{Q_a} + \frac{Q_B}{Q_b} = \text{synergy index}$$

where:
$Q_a$=quantity of APG, acting alone, producing an endpoint.
$Q_b$=quantity of biocide, acting alone, producing an endpoint.
$Q_A$=quantity of APG in mixture, producing an endpoint.
$Q_B$=quantity of biocide in mixture, producing an endpoint.

If the Synergy Index is
<1, it indicates synergy
=1, it indicates additivity
>1, it indicates antagonism Instead of using the conventional plate enumeration method, a bacterial luminescent test was employed to calculate the endpoints. A decrease in light emission depends on toxicant concentration in the test and is used to calculate the relative toxicity unit (RLU). This test gives rapid and sensitive detection of toxicants compared to conventional minimal inhibitory concentration (MIC) assays. Table 4 lists the synergy indices of several combinations of APG and stabilized bromine-based biocide (STB) tested in the laboratory. The concentrations expressed are mg/L for APG as active ingredient and mg/L as total chlorine for STB. The results shown in Table 4 demonstrate that all the APG/STB combinations tested were synergistic. It should be noted that APG by itself did not show significant toxicity to reduce bioluminescence readings. However, when combined with the biocides, APG dramatically improved the antimicrobial activity.

TABLE 4

| STB (ppm TRO*) | Alkyl Polyglycoside (ppm) | | | | |
|---|---|---|---|---|---|
| | 2.5 | 5 | 7.5 | 10 | 15 |
| 0.1 | 0.61 | 0.27 | 0.92 | 0.33 | 0.41 |
| 0.2 | 0.36 | 0.26 | 0.66 | 0.04 | 0.07 |
| 0.5 | 0.16 | 0.26 | 0.33 | 0.05 | 0.19 |
| 1.0 | 0.08 | 0.15 | 0.16 | 0.02 | 0.06 |
| 2.0 | 0.05 | 0.05 | 0.05 | 0.02 | 0.04 |
| 5.0 | 0.02 | 0.04 | 0.03 | 0.02 | 0.02 |

*TRO = Total Residual Oxidant (referring to chlorine here)

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

What is claimed is:

1. A method of removing biofilms from surfaces submerged in a fouled water system comprising the step of adding to the water system an effective amount of an alkyl polyglycoside having the chemical formula:

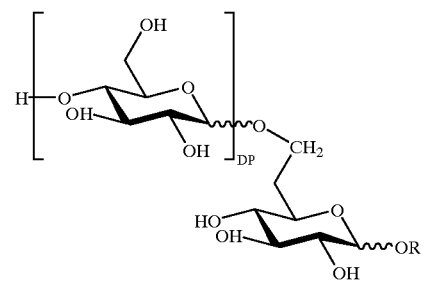

wherein R is a $C_8$–$C_{16}$ alkyl chain and DP is from 0 to 3 carbohydrate units.

2. The method of claim 1 wherein the alkyl chain is linear.

3. The method of claim 1 wherein DP is from about 1.1 to 1.5.

4. The method of claim 1 wherein the alkyl polyglycoside is added to the water system in an amount of from about 0.1 ppm to about 50 ppm.

5. The method of claim 1 wherein the alkyl polyglycoside is added to the water system in an amount of from about 1 ppm to about 10 ppm.

6. The method of claim 1 wherein the water system is an industrial water system.

7. The method of claim 1 wherein the water system is a recreational water system.

8. The method of claim 1 wherein a biocide is optionally added to the water system.

9. The method of claim 8 wherein the biocide is an oxidizing biocide.

10. The method of claim 8 wherein the biocide is a non-oxidizing biocide.

11. A method of removing biofilms from surfaces submerged in a fouled water system comprising the step of adding to the water system an effective amount of a biocide and an alkyl polyglycoside having the chemical formula:

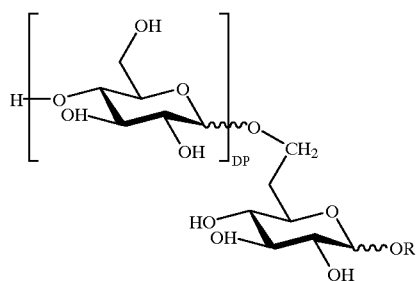

wherein R is a $C_8$–$C_{16}$ alkyl chain and DP is from 0 to 3 carbohydrate units.

12. The method of claim 11 wherein the alkyl chain is linear.

13. The method of claim 11 wherein DP is from about 1.1 to 1.5.

14. The method of claim 11 wherein the alkyl polyglycoside is added to the water system in an amount of from about 0.1 ppm to about 50 ppm.

15. The method of claim 11 wherein the alkyl polyglycoside is added to the water system in an amount of from about 1 ppm to about 10 ppm.

16. The method of claim 11 wherein the water system is an industrial water system.

17. The method of claim 11 wherein the water system is a recreational water system.

18. The method of claim 11 wherein the biocide is an oxidizing biocide.

19. The method of claim 11 wherein the biocide is a non-oxidizing biocide.

* * * * *

UNITED STATES PATENT AND TRADEMARK OFFICE
CERTIFICATE OF CORRECTION

PATENT NO.   : 6,080,323  
DATED        : June 27, 2000  
INVENTOR(S)  : F. Philip Yu and Anthony W. Dallmier Page 1 of 1

It is certified that error appears in the above-identified patent and that said Letters Patent is hereby corrected as shown below:

Please delete the chemical formula in the ABSTRACT,  
Column 2, Line 10 and Line 40  
Column 6, Line 47  
Column 7, Line 19  
and substitute therefor the following:

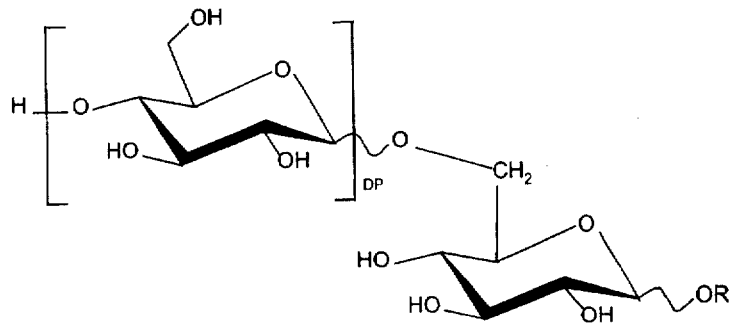

Signed and Sealed this

Ninth Day of April, 2002

Attest:

JAMES E. ROGAN  
Attesting Officer   Director of the United States Patent and Trademark Office